US010692396B2

(12) United States Patent
Bitran et al.

(10) Patent No.: US 10,692,396 B2
(45) Date of Patent: Jun. 23, 2020

(54) CALCULATING CALORIE STATISTICS BASED ON PURCHASES

(71) Applicant: Microsoft Technology Licensing, LLC, Redmond, WA (US)

(72) Inventors: Hadas Bitran, Ramat Hasharon (IL); Todd Holmdahl, Redmond, WA (US); Eric Horvitz, Kirkland, WA (US); Desney S. Tan, Kirkland, WA (US); Dennis Paul Schmuland, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 375 days.

(21) Appl. No.: 14/963,032

(22) Filed: Dec. 8, 2015

(65) Prior Publication Data

US 2017/0039886 A1  Feb. 9, 2017

Related U.S. Application Data

(60) Provisional application No. 62/202,113, filed on Aug. 6, 2015.

(51) Int. Cl.
*G09B 19/00* (2006.01)
*G09B 5/02* (2006.01)
(Continued)

(52) U.S. Cl.
CPC ....... *G09B 19/0092* (2013.01); *G06F 3/0482* (2013.01); *G06F 3/04847* (2013.01);
(Continued)

(58) Field of Classification Search
CPC ........... G09B 19/00; G09B 5/02; G06F 17/60; G06F 19/3478; G06F 3/0482; G06F 3/167
See application file for complete search history.

(56) References Cited

U.S. PATENT DOCUMENTS

| 6,675,041 B2 | 1/2004 | Dickinson |
| 7,769,635 B2 * | 8/2010 | Simons-Nikolova ....................... G01G 19/4146 235/462.46 |

(Continued)

FOREIGN PATENT DOCUMENTS

| CA | 2009700 A1 | 8/1991 |
| EP | 2518649 A1 | 10/2012 |

(Continued)

OTHER PUBLICATIONS

Buytendijk, F. et al., "Summary and Link to Purchase 'Analytics Gets Personal with the Quantified Self'," Gartner, Inc. Website, Available Online at https://www.gartner.com/doc/2487617?ref=ddisp, May 17, 2013, 2 pages. (Applicant finds no readily available full copy; USPTO encouraged to obtain its own copy).

(Continued)

*Primary Examiner* — Robert J Utama
(74) *Attorney, Agent, or Firm* — Alleman Hall Creasman & Tuttle LLP (57) ABSTRACT

A computing system for calculating a total calorie count is provided. The computing system comprising an electronic personal assistant application program executed on a client computing device, and including a purchase tracking module configured to receive notifications of purchases made for individual food items, a calorie tracking module configured to identify calorie counts associated with each purchased food item and to calculate a calorie count statistic based thereon, a calorie apportionment module configured to apportion the calorie counts of the food items to a user so that the calorie count statistic is based upon an apportioned total of the calorie counts of the food items that have been apportioned to the user; and a graphical user interface module configured to display a graphical user interface (Continued)

including an indicator of the calorie count statistic on a display associated with the client computing device.

20 Claims, 6 Drawing Sheets (51) Int. Cl.
    *G06Q 50/22*      (2018.01)
    *G16H 20/60*      (2018.01)
    *G06F 3/0482*      (2013.01)
    *G06F 3/0484*      (2013.01)
    *G06F 3/16*      (2006.01)
    *G06Q 30/06*      (2012.01)

(52) U.S. Cl.
    CPC ......... *G06F 3/167* (2013.01); *G06Q 30/0633* (2013.01); *G06Q 50/22* (2013.01); *G09B 5/02* (2013.01); *G16H 20/60* (2018.01)

(56) References Cited

U.S. PATENT DOCUMENTS

| | | | |
|---|---|---|---|
| 8,655,717 B2 | 2/2014 | Schwarzberg et al. | |
| 8,924,239 B1 | 12/2014 | Kurple | |
| 9,011,153 B2 | 4/2015 | Bennett et al. | |
| 9,042,596 B2 | 5/2015 | Connor | |
| 2001/0032184 A1 | 10/2001 | Tenembaum | |
| 2002/0027164 A1* | 3/2002 | Mault | A61B 5/1118 235/462.46 |
| 2003/0208409 A1 | 11/2003 | Mault | |
| 2005/0049920 A1 | 3/2005 | Day et al. | |
| 2005/0113649 A1* | 5/2005 | Bergantino | G06F 19/3475 600/300 |
| 2007/0050058 A1 | 3/2007 | Zuziak et al. | |
| 2007/0055573 A1* | 3/2007 | Grell | G06Q 20/209 705/24 |
| 2008/0086374 A1* | 4/2008 | Aitken | G06F 19/3475 705/14.27 |
| 2009/0075242 A1* | 3/2009 | Schwarzberg | G09B 19/0092 434/127 |
| 2009/0099873 A1* | 4/2009 | Kurple | G06Q 50/24 705/3 |
| 2009/0192901 A1 | 7/2009 | Egeresi | |
| 2010/0003653 A1 | 1/2010 | Brown | |
| 2010/0305848 A1 | 12/2010 | Stallman | |
| 2011/0272474 A1 | 11/2011 | Mullen et al. | |
| 2012/0021388 A1 | 1/2012 | Arbuckle et al. | |
| 2012/0083669 A1* | 4/2012 | Abujbara | G06F 19/3475 600/300 |
| 2012/0094258 A1* | 4/2012 | Langheier | G06F 19/3475 434/127 |
| 2012/0183932 A1 | 7/2012 | Chang et al. | |
| 2012/0315609 A1* | 12/2012 | Miller-Kovach | G09B 19/0092 434/127 |
| 2012/0330781 A1 | 12/2012 | Borrero | |
| 2013/0024282 A1 | 1/2013 | Kansal et al. | |
| 2013/0273506 A1 | 10/2013 | Melowsky | |
| 2014/0080102 A1 | 3/2014 | Krishna | |
| 2014/0195359 A1 | 7/2014 | Schulz | |
| 2014/0195556 A1 | 7/2014 | Fan | |
| 2015/0066687 A1 | 3/2015 | Blackhurst et al. | |

FOREIGN PATENT DOCUMENTS

| | | |
|---|---|---|
| WO | 2007081967 A2 | 7/2007 |
| WO | 2013192452 A2 | 12/2013 |
| WO | 2014008555 A1 | 1/2014 |

OTHER PUBLICATIONS

McIntyre, A. et al., "Summary and Link to Purchase 'Market Trends: Enter the Wearable Electronics Market With Products for the Quantified Self'," Gartner, Inc. Website, Available Online at https://www.gartner.com/doc/2537715?ref=ddisp, Jul. 1, 2013, 2 pages. (Applicant finds no readily available full copy; USPTO encouraged to obtain its own copy).

Gotta, S., "Summary and Link to Purchase 'Technology Overview: Quantified Self'," Gartner, Inc. Website, Available Online at https://www.gartner.com/doc/2591327?ref=ddisp, Sep. 17, 2013, 2 pages. (Applicant finds no readily available full copy; USPTO encouraged to obtain its own copy).

Dunbrack, L., "Abstract and Link to Purchase 'Perspective: The Consumer Experience—Why Consumers Stop Using Fitness Trackers'," IDC Research, Inc. Website, Available Online at http://www.idc.com/getdoc.jsp?containerId=HI249613, Jun. 2014, 2 pages. (Applicant finds no readily available full copy; USPTO encouraged to obtain its own copy).

"Calorie Counter", Published on: Aug. 19, 2013, Available at: https://play.google.com/store/apps/details?id=com.about.CalorieCount&hl=en.

"Consumer Decision Journey: Health and Wellness", Retrieved on: Aug. 17, 2015 Available at: http://advertising.microsoft.com/en/cl/6933/consumer-decision-journey-health-and-wellness.

Tozzi, et al., "Bloomberg: Your Google searches could help the FDA find drug side-effects", Published on: Jul. 15, 2015 Available at; http://www.bloomberg.com/news/articles/2015-07-15/your-google-searches-could-help-the-fda-find-drug-side-effects.

"NuMi", Retrieved on: Aug. 20, 2015 Available at: https://play.google.com/store/apps/details?id=com.nutrisystem.numi&hl=sl.

Johnson, et al., "A Mobile Food Recommendation System Based on the Traffic Light Diet ", In Journals of the Computing Research Repository, Sep. 2014, 8 pages.

ISA European Patent Office, International Search Report and Written Opinion Issued in Application No. PCT/US2016/043222, dated Sep. 23, 2016, WIPO, 10 Pages.

\* cited by examiner

CALCULATING CALORIE STATISTICS BASED ON PURCHASES

CROSS REFERENCE TO RELATED APPLICATIONS

This application claims priority to U.S. Provisional Patent Application No. 62/202,113, filed Aug. 6, 2015, the entirety of which is hereby incorporated herein by reference.

BACKGROUND

Improving one's health is a goal that most individuals share, yet many people fall short in achieving. In our busy lives, it can be difficult to make time to visit health care providers for check ups and preventative care. And, many people have trouble following through with resolutions to eat well and exercise. It can also be difficult for people who are not feeling well to understand the causes behind their conditions. Significant challenges exist to improving the health and well-being of both individuals and entire populations, which the technological solutions described herein offer the promise of addressing.

SUMMARY

To address the issues discussed above, a computing system for calculating a calorie count statistic is provided. The computing system comprising an electronic personal assistant application program executed on a client computing device, and including: a purchase tracking module configured to receive notifications of purchases made for individual food items, a calorie tracking module configured to identify calorie counts associated with each purchased food item and to calculate a calorie count statistic based thereon, a calorie apportionment module configured to apportion the calorie counts of the food items to a user by receiving a user apportionment input and apportioning the calorie counts by the user apportionment input, and applying a predetermined apportionment formula to the calorie counts, so that the calorie count statistic is based upon an apportioned total of the calorie counts of the food items that have been apportioned to the user; and a graphical user interface module configured to display a graphical user interface including an indicator of the calorie count statistic on a display associated with the client computing device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
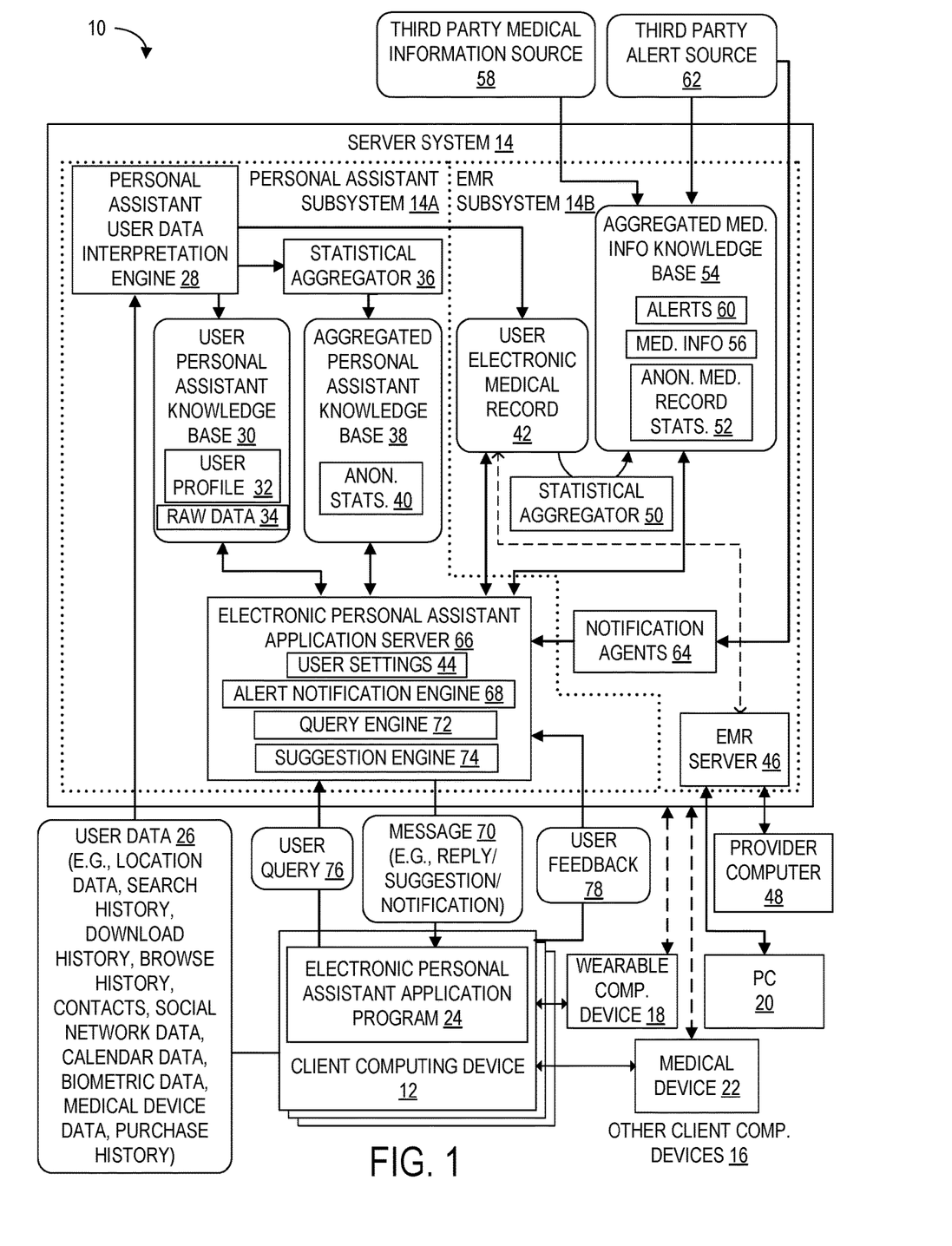
FIG. 1 shows an example computing system according to an embodiment of the present description.

FIG. 1 illustrates a computing system 10 according to one embodiment of the present disclosure. As shown, computing system 10 includes a client computing device 12, which, for example, may take the form of a smart phone or tablet computing device, configured to communicate via a computer network with a server system 14. Computing system 10 may also include other client computing devices 16 configured to communicate with the server system directly through a network connection or indirectly through the client computing device 12. The other client computing devices 16 may include a wearable computing device 18, which may take the form of a wrist mounted device or head mounted device, a personal computer 20, which may take the form of a laptop or desktop computer, and a computerized medical device 22, such as a computerized pulse oximeter, electronic inhaler, electronic insulin delivery device, electronic blood sugar monitor, blood pressure monitor, etc. Wearable computing devices may also include sensors embedded in clothing (t-shirts, undergarments, etc.), or mounted to other body parts (e.g., a finger or ear lobe). Also envisaged are Internet of Things (TOT) devices not worn directly on the body, but arranged in physical proximity to the user. Such devices may allow measurement of biometric and other data. Examples include cameras, far-infrared thermal detectors, and under-the-mattress sleep sensors, etc. Herein, where functions of the client computing device 12 are described, it will be appreciated that any of the other client computing devices 16 may function in the same manner, unless the specific form factor of the device is mentioned explicitly.

Client computing device 12 is configured to execute an electronic personal assistant application program 24. It will be appreciated that other instances of the electronic personal assistant application program 24 may be executed on the other client computing devices 16 as well, all of which are associated with a user account on server system 14. Subject to authorization by a user, the electronic personal assistant program is configured to passively monitor various user data 26 on the client computing device 12 and other client computing devices 16, such as location data, search history, download history, browsing history, contacts, social network data, calendar data, biometric data, medical device data, purchase history, etc.

Specific examples of these various types of user data 26 will now be described. Location data may include for example, GPS coordinate data (latitude and longitude) obtained by a GPS receiver implemented on any client computing device, an identifier such as an IP address and/or Wi-Fi access point identifier that can be resolved to a generalized geographic location, a user check-in at a location via a social network program, etc. Search history may include a user's search queries entered in a search engine interface such as a browser displaying a search engine web page or a search application executed on the client computing device. The download history may include, for example, applications installed, or files downloaded from a download website, including songs, videos, games, etc. Each of these applications and files may have metadata associated with them, such as categories, genres, etc., which can be used to build user profile 32, discussed below. The browse history may include a list of websites, and particular pages within websites visited by a user using a browser executed on the client computing device. The browse history may also include in-application browsing of application specific databases, such as a shopping application that is configured to enable a user to browse a vendor's catalog. The contacts include names and contact information for individuals or organizations saved in a user contact database on client computing device 12, or retrieved from an external site, such as a social network website. The social network data may include a user's friends list, a list of social network entities "liked" by the user, check-ins made by the user at locations via a social network program, posts written by the user, etc. Biometric data may include a variety of data sensed by sensors on client computing device 12 or other client computing devices 16, such as pedometer information, heart rate and blood pressure, duration and timing of sleep cycles, body temperature, galvanic skin response, etc. Additional biometric data is discussed below in relation to the wristwatch embodiment of the wearable computing device 18. Medical device data may include data from medical device 22. Such data may include, for example, inhaler usage data from an electronic inhaler device, blood sugar levels from an electronic blood sugar monitor, insulin pumping data from an electronic insulin pump, pulse oximetry data from an electronic pulse oximeter, etc. Purchase history may include information gleaned from an ecommerce transaction between the client computing device 12 and an ecommerce platform, regarding products purchased by a user, including product descriptions, time and date of purchase, price paid, user feedback on those purchases, etc. It will be appreciated that these specific examples are merely illustrative and that other types of user data specifically not discussed above may also be monitored.

User data 26 is transmitted from the electronic personal assistant application program 24 to the personal assistant inference engine 28 executed on server system 14. The personal assistant user data inference engine 28 performs various operations on the received user data 26, including storing copies the raw data 34 of the user data 26 in the user personal assistant knowledge base 30 (a database stored in a mass storage device of the server system 14), making inferences based upon the received user data 26 to thereby fill out a user profile 32 for the user, passing some of the user data 26 for each individual user to a statistical aggregator 36, which computes anonymized statistics 40 based on information received from all users of the server system and stores these anonymized statistics in the aggregated personal assistant knowledge base 38 (another databases stored in a mass storage device of the server system 14), and passing a filtered subset of the user data to the user electronic medical record 42 based on user settings 44 in the electronic personal assistant application server 66.

As a specific example, the user profile may include inferred data from the user data 26 regarding the demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, and health benefits information.

User electronic medical records are secure electronic records stored in a database in a mass storage device associated with server system 14. Typically, data is populated within the electronic medical record for each user by a healthcare provider using provider computer 48. Provider computer 48 interacts with secure electronic medical record server 46, which in turn stores and retrieves the data in the user electronic medical record 42. The EMR server is configured to communicate with secure channels (e.g., HTTPS and TLS), and store data in encrypted form. Further, the EMR server is configured to control access to the user electronic medical record such that only authorized healthcare providers can make entries and alter certain provider-controlled fields of the medical record. Provider controlled fields may include many of the same types of data included in the user profile, but which are confirmed with the user by the provider and entered into the medical record by the provider rather than inferred by computer algorithms, thus the accuracy and provenance of the data in the EMR is greater than the user profile 32. Specific examples of data that may be stored in the provider controlled portion of the user electronic medical record include demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, health benefits information, and genetic profile of the user.

Other fields within the user electronic medical record are user-controlled, such that authorized persons including the patient who is the subject of the medical record can make entries in the medical record. Further, the user may adjust user settings 44 to allow the personal assistant user data interpretation engine 28 to programmatically update the user-controlled fields of the user electronic medical record with either raw data 34 or inferred data in user profile 32 derived from user data 26. In this way the medical record may be programmatically updated to include medical device data such as inhaler usage, blood sugar monitoring levels, insulin pump usage, etc., and biometric data such as heart rate and blood pressure history, sleep history, body temperature, galvanic skin response, etc.

A statistical aggregator 50 is provided to generate anonymized medical records statistics 52 based on the stored user electronic medical records of an entire user population or a predefined cohort thereof, and store the anonymized medical record statistics in aggregated medical information knowledge base 54. In this manner, statistics may be stored for all manner of user populations. For example, a percentage of the population who live within a defined geographical region and who have been diagnosed with a certain medical condition (such as H1N1 influenza) may be identified, and data about this subset of persons may be compared to identify risk factors. The statistical aggregator may also process statistics related to steps, calories, activity level, sleep and exercise habits of an entire population, or a predefined cohort thereof, which later may be used for comparative insights on user behaviors.

Medical information 56 aggregated from third party medical information sources 58 and alerts 60 from third party alert sources 62 are also stored within the aggregated medical information knowledge base 54. In other implementations, the aggregated medical information need not be stored per se, provided it can be accessed in real time. Examples of medical information 56 includes current practices and procedures, differential diagnostic information that medical professionals use to distinguish between possible diagnoses for a given set of symptoms, descriptions of medical conditions including diseases and syndromes, and their associated symptoms, information on standardized medical screenings recommended by age and gender of the patient, information on standardized vaccination schedules recommended for children and adults, medical conditions associated with certain genetic profiles, drug information such as doses, allergens, potential interactions, etc. Examples of third party medical sources 58 include medical publishers, professional medical organizations. Examples of alerts include reports from governmental and non-governmental organizations that report the occurrence of disease in particular geographic regions, including the boundaries of the geographic region, the type of disease reported, the number of persons affected, the mortality statistics associated with the affected persons, information about the incubation period and period of contagiousness for the disease, and any travel restrictions or recommended restrictions to the affected geographic region, etc. These alerts may be from a country's center for disease control, state or county health department, a company, a school district, a hospital, etc.

Alerts 60 from third party alert sources 62 may also be received by notification agents 64 within server system 14, which in turn instruct an alert notification engine 68 of the electronic personal assistant application server 66 to send a message 70 in the form of a push notification featuring the content of the alert 60 to the electronic personal assistant application program 24 executed on the client device 12, or multiple client devices running the personal assistant application program. In one specific example, the alert may be sent only to users who have recently traveled to the affected area, or who the data interpretation engine 28 infers will soon travel to the affected area, to inform the person of a disease outbreak in the particular geographic area. In another example, the alert may be sent to only to persons who have been detected by the system as being within a threshold distance of a person who has been diagnosed with a contagious disease throughout the period which the diagnosed person was contagious. Such a notification can be made while maintaining the privacy of the diagnosed individual.

In addition to push notifications for alerts 60, electronic personal assistant application server 66 also includes a query engine 72 configured to respond with messages 70 in the form of replies to a user query 76 received from the electronic personal assistant application program, and a suggestion engine 74 configured to proactively send messages 70 in the form of suggestions to the electronic personal assistant application programs based on user settings 44 and a set of programmatic suggestion rules. In one specific example, the client computing device 12 may display a query interface, such as a text box or voice prompt, and the user may type in a query or speak a query to the client computing device, such as "What could be causing this headache?" This user query 76 is sent to the query engine 72, which performs searches in each of the databases 30, 38, 42, and 52, subject user authorizations via settings 44 to conduct searches using each of these databases. Results are returned from each database relating to causes for headaches. The user profile may indicate that the user is a "coffee drinker," and the purchase history and location history may indicate the user visits coffee shops on average 2-3 times a day but has not visited a coffee shop in the past 2 days. The anonymized statistics may indicate that "coffee drinkers" report having headaches more often than the general population. The user electronic medical record may include a prior doctor visit in which the complained of a headache after suffering from heatstroke. The aggregated medical information knowledge base may contain medical information that indicates that heatstroke is typically experienced when a user sweats profusely in extremely hot temperatures and experiences fast heartbeat. The raw data 34 from the user profile may show extremely hot ambient temperatures but may not show galvanic skin response indicative of sweating nor a pulse indicative of fast heartbeat. In this case the query engine would apply weightings that result in ranking the possible causes of the headache as (1) caffeine withdrawal, and (2) heat exhaustion, and display this information to the user with a recommendation to seek the advice of a health care professional.

The electronic personal assistant application program may solicit user feedback 78 from the user regarding the effectiveness or appropriateness of the message 70, which may in turn be transmitted back to the electronic personal assistant application server 66, and used by machine learning algorithms executed thereon to continually improve the weightings and logic by which the electronic personal assistant application server 66 makes decisions regarding the content to send to the client computing device in message 70. Continuing with the above example, if the user's headache was in fact caused by caffeine withdrawal, as diagnosed during a visit to a healthcare professional, the user might enter feedback indicating the first displayed search result was correct, and that information could then be passed to the query engine 72 as a confirmed result for machine learning algorithms that strengthen the weightings upon which the ranking was based when such confirmations are received.

Figure 2:
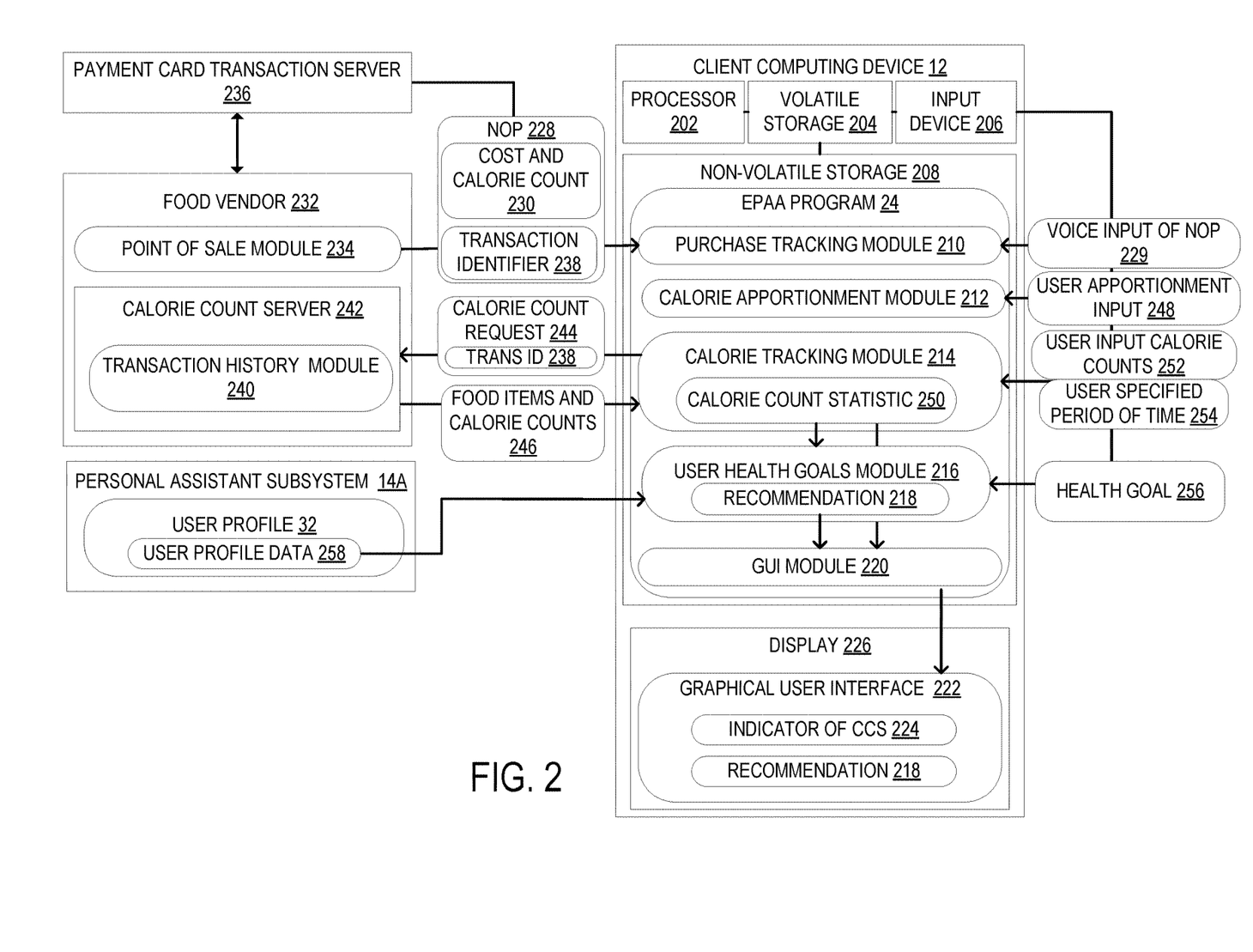
FIG. 2 shows a computing system for calculating a calorie count statistic using the computing system of FIG. 1.

FIG. 2 shows a use-case example of computing system 10 for calculating a calorie count statistic for a user of the client computing device 12. The calorie count statistic may, for example, be a total calorie count over a time period, an average calorie count for repeating time periods, a remaining calorie count before a maximum or minimum threshold is reached for a time period, etc. The client computing device 12 includes a processor 202, a volatile storage 204, an input device 206, and a non-volatile storage 208. The non-volatile storage 208 stores instructions for the electronic personal assistant application program 24 executed on the client computing device 12, and including a purchase tracking module 210 configured to receive notifications of purchases 228 made for individual food items, a calorie apportionment module 212 configured to apportion the calorie counts of the food items to a user, a calorie tracking module 214 configured to identify calorie counts associated with each purchased food item and to calculate a calorie count statistic based thereon, a user health goals module 216 for storing user specified health goals and determining a recommendation 218, and a graphical user interface module 220 configured to display a graphical user interface 222 including an indicator of the calorie count statistic 224 and the recommendation 218 on a display 226 associated with the client computing device 12.

In one embodiment, the notifications of purchases 228 are electronic receipts that include a cost and a calorie count 230 for each purchased food item. In this embodiment, the electronic receipts are received from a food vendor 232. The food vendor may be a restaurant, a grocery store, or an online food vendor as a few non-limiting examples. The notifications of purchases 228 may be received from a point of sale module 234 of the food vendor 232. In one specific example, the client computing device 12 is a smart phone that is configured to receive the notifications of purchases 228 via a near field connection with the point of sale module 234, which may be an electronic point of sale device. However, it will be appreciated that the notifications of purchases 228 may be received via other methods, such as an email message, a text message, or an in-app message as a few non-limiting examples. In another example, the client computing device 12 may be configured to receive the notifications of purchases 228 from a payment card transaction server 236, which may be a server associated with the user's payment card, such as a debit card or a credit card.

In another embodiment, the notifications of purchases 228 are electronic receipts that include a transaction identifier 238. In this embodiment, the point of sale module 234 of the food vendor 232 may be configured to tag each transaction with a unique transaction identifier 238, and store a list of food items that were purchased in the transaction along with the associated transaction identifier 238, in a transaction history module 240 executed on a calorie count server 242 of the food vendor 232. In this embodiment, the calorie tracking module 214 is configured to send a calorie count request 244 to the calorie count server 242 including the transaction identifier 238, and receive from the calorie count server 242 the list of food items associated with the transaction identifier 238 and calorie counts 246 for each food item in the list.

In another embodiment, the notifications of purchases are voice inputs 229 from the user that indicate a purchased food item. The voice input 229 may be received by the client computing device 12 via the input device 206, which may be a microphone in this embodiment. For example, the user may enter a voice input 229 to the client computing device 12 by saying "I just ate a burger from Food Chain A". Next, the calorie tracking module 214 may be configured to query a food database to retrieve calorie counts for the burger from Food Chain A. If calorie counts for the burger from Food Chain A cannot be retrieved, the calorie tracking module 214 may utilize a fuzzy matching system that estimates calorie counts based on the purchased food items. For example, the calorie tracking module 214 may query the food database to retrieve calorie counts for a burger from Food Chain B, which may be estimated to have a similar calorie count as the burger from Food Chain A.

In another example, the voice input 229 may be the user saying "I just ate a burger", without specifying a food vendor 232 from which the burger was purchased by the user. In one embodiment, the purchase tracking module 210 may be further configured to track and store the user's purchase history and visited food vendors 232 with respect to the user's location at the time of the purchase. The user's history of purchased food items and visited food vendors may also be sent to the personal assistant subsystem 14A to be stored in the user profile 32 of the user personal assistant knowledge base 30. Additionally, the personal assistant user data interpretation engine 28 may be further configured to determine nutrition behavior and patterns of the user based on the history of purchased food items and associated food vendors visited by the user. This data regarding nutrition behavior and patterns of the user may also be stored in the user profile 32 of the user personal assistant knowledge base 30.

Thus, when the user enters the voice input 229 of "I just ate a burger", the purchase tracking module 210 may be further configured to retrieve user profile data including nutrition behavior and patterns of the user determined based on a history of purchased food items and associated food vendors that may be stored in the purchase tracking module 210 or retrieved from the user profile 32 of the user personal assistant knowledge base 30. Next, the purchase tracking module 210 may be configured to identify calorie counts for the purchased food item of the voice input 229 based on the retrieved history of purchased food items and associated food vendors. For example, the user may have a history of eating burgers from Food Chain A. Thus, the purchase tracking module 210 may then identify calorie counts for the food item of the "I just ate a burger" voice input 229 as the calorie counts for a burger from Food Chain A.

Alternatively, the calorie tracking module 214 may utilize a crowdsourcing method to identify calorie counts. For example, if the calorie tracking module 214 is not able to retrieve calorie counts for the burger from Food Chain A, the client computing device 12 may be configured to ask the user to input the calorie counts for the burger via the input device 206. The entered calorie counts for the burger from Food Chain A may then be sent by the client computing device 12 to the personal assistant subsystem 14A. In this example, personal assistant subsystem 14A of the server system 14 may aggregate the calorie count for the burger from Food Chain A entered by the user with other calorie counts for other food items entered by other users of other client computing devices also associated with server system 14. In this way, personal assistant subsystem 14A may crowdsource calorie counts for various food items and store these calorie counts in the aggregated personal assistant knowledge base 38, such that these calorie counts may be retrieved by the client computing device 12 of the user.

In some cases, the notifications of purchases 228 may include additional food purchases for people other than the user of the client computing device 12. For example, the user may be buying groceries for the user's family, or may be dining out at a restaurant with the user's family. For these cases, the list of food items and calorie counts (230 or 246) may be sent to the calorie apportionment module 212 configured to apportion the calorie counts of the food items 246 to the user by receiving a user apportionment input 248 and apportioning the calorie counts by the user apportionment input 248, and applying a predetermined apportionment formula to the calorie counts, so that the calorie count statistic 250 is based upon an apportioned total of the calorie counts of the food items 246 that have been apportioned to the user. In one embodiment, the user apportionment input may be an input to select food items from the list of food items that the user of the client computing device 12 actually ate. In this embodiment, the graphical user interface module 220 is further configured to display an itemized list of the food items and associated calorie counts 246, and the user apportionment input 248 is a user selection input of a food item. Accordingly, the calorie apportionment module 212 adds only the calorie counts associated with the selected food items to the calorie count statistic.

In another embodiment, the apportionment input 248 is a user input of a ratio of the food items consumed by the user. For example, the user may input that 30% of the food items were consumed by the user. This ratio may then be applied to the total calorie counts of the food items, which may then be added to the user's calorie count statistic 250.

In another embodiment, the calorie apportionment module may apportion the calorie counts of the food items based on physical characteristics of the user and the other people who also ate the food. For this embodiment, the user apportionment input 248 is a user input of a list of people that consumed the food items, and the predetermined apportionment formula is a ratio of the user's body weight compared to a total body weight of the list of people. Thus, the calorie counts may be automatically apportioned to the user based on the user's weight compared to the weight of the other people who also ate the food. The user's body weight may be retrieved from the user profile 32 of the user personal assistant knowledge base 30 of personal assistant subsystem 14A. In one specific example, the total body weight of the list of people may be determined by a user input of each person's body weight. In another example, each person in the list of people may have their own user profile 32 in the server system 14. Thus, the client computing device 12 may query the server system 14 to request access to and retrieve each person's body weight stored in their respective user profiles. It will be appreciated that other characteristics of the user may be used to apportion the calorie counts, such as a history of eating habits of the user. Additionally, it will be appreciated that the user apportionment input 248 may be entered by the user via a variety of input methods, such as a touch input, voice input, or a gesture input as a few non-limiting examples.

The predetermined apportionment formula applied to the calorie counts will depend upon the type of apportionment input entered by the user. For example, if the user apportionment input is a selection of the food items eaten by the user, then the predetermined apportionment formula will add the calorie counts of the selected food items to the calorie count statistic 250, which in this case is a calorie count total. In another example, if the user apportionment input is a list of people who ate the food items, then the user apportionment input may be a weighting factor, such as 30%, which adds a portion of the aggregated calorie counts of the list of food items to the user's total calorie counts based on the weight of the user compared to the combined weight of the other people in the list of people entered by the user.

Based on the apportioned calorie counts, the calorie tracking module 214 calculates a calorie count statistic 250 that indicates a total calorie count for the user of the client computing device 12. In addition to the apportioned calorie counts, the user may also manually enter additional calorie counts. For example, if the user eats a food item that was not purchased, or the food vendor 232 is not set up for sending the notification of purchases 228, the user may manually enter user input calorie counts 252 that are sent to the calorie tracking module 214 of the client computing device 12. These user input calorie counts 252 may be added to the calorie count statistic 250 that indicates the total calories for the user. In one embodiment, the calorie tracking module 214 is configured to calculate the calorie count statistic 250 for a user-specified period of time 254. For example, the user specified period of time may be 6 hours, 12 hours, a day, a week, a month, or any other suitable period of time. It will be appreciated that the user may enter the user-specified period of time through a variety of input methods, such as a voice input, a touch input, or a gesture input as a few non-limiting examples.

The calorie count statistic 250 is sent to the user health goals module 216 executed on the client computing device 12. The user health goals module 16 is configured to receive user input of a health goal 256 from a user. In one specific example, the health goal is an amount of weight that the user has a goal of losing. In another example, the health goal is a maximum total calorie count for each day that the user wishes to be under. However, it will be appreciated that any suitable health goal 256 may be entered by the user. Next, the user health goals module 216 is further configured to determine a recommendation based upon the user inputted health goal 256 and the calorie count statistic 250. For example, if the user inputted health goal 256 was a maximum total calorie count for the day, then the user health goals module 216 may be configured to subtract the total calorie count from the maximum total calorie count for the day to calculate how many calories the user may eat for the next meal and still achieve the user inputted health goal 256.

In one embodiment, the recommendation 218 is a food item recommendation. For example, the user health goals module 216 may determine a recommendation 218 for food the user may eat to achieve the user inputted health goal 256. In the above maximum total calorie count example, the food item recommendation may be a food item that the user could eat at the next meal that will keep the user's total calorie count under the maximum total calorie count of the day that is specified by the user inputted health goal 256. However, it will be appreciated that the recommendation 218 may be determined based on a variety of factors. In one embodiment, the food item recommendation is determined based upon user profile data 258 associated with a user profile 32. The user profile 32 may be stored and managed via the personal assistant subsystem 14A described above. Thus, the user profile data may include health data, exercise data, biometric feedback, consumption patterns, GPS trends, and any other data collected, aggregated and analyzed by the personal assistant subsystem 14A. In one specific example, the food item recommendation is determined based upon user medical data included in the user profile 32. Thus, if the user has a medical condition, such as Celiac Disease, the user health goals module 216 may determine an appropriate food item recommendation, such as gluten-free food in this example. It will be appreciated that the determination may be made either on the client computing device 12, or may be made by sending a request for a recommendation to the personal assistant subsystem 14A, and then receiving the recommendation from the personal assistant subsystem 14A.

In another embodiment, the food item recommendation is determined based upon availability of food items from vendors in proximity to the user's expected location at a next meal time. The user's expected location at a next meal time may be determined through a variety of means. For example, the user may input a destination for dinner, such as "at home" or "downtown", and the client computing device 12 may send requests to food vendors in proximity to the destination, and receive lists of food items and calorie counts. Based on the received food items and calorie counts from the proximate food vendors, the user health goals module 216 may determine a recommendation of a food item from a food vendor that is both proximate to where the user is heading as well as suitable to achieve the user inputted health goal 256. In another example, the user profile data 258 may include GPS trends of the user of the client computing device 12. In one specific example, the user may typically head "downtown" for dinner every Friday. Thus, the user's expected location at a next meal time may be "downtown" if it is currently Friday and the next meal time is dinner. Accordingly, the client computing device 12 may retrieve food item lists and calorie counts from food vendors in proximity to "downtown", and determine a food item recommendation based thereon.

In another embodiment, the food item recommendation is determined based on user profile data 258 associated with the user profile 32, the user profile data 258 including nutrition behavior and patterns of the user determined based on a history of purchased food items and associated food vendors. The nutrition behavior and patterns being stored being aggregated, interpreted, and stored in the user profile 32 as discussed previously. For example, the user health goals module 216 may determine that the user tends to dine at fast food chains based on the stored nutrition behavior and patterns. Thus, in this specific example, the user health goals module 216 may be configured to determine a food item recommendation to eat Healthy Food Item A from the Organic Food Vendor A.

In another embodiment, the recommendation 218 is an exercise recommendation. In one specific example, if the calorie count statistic 250 is too high to achieve the user inputted health goal 256, then the user health goals module 216 may be configured to determine an exercise recommendation for the user. The exercise recommendation may be determined based on the user profile data 258. For example, the user profile data 258 may include data that suggests that the user prefers biking to running. Thus, the user health goals module 216 may determine an exercise recommendation for the user to bike a certain distance that will achieve the user inputted health goal 256. In one specific example, if the total calorie count 250 is 500 calories above the user inputted health goal, then the user health goals module 216 may determine an exercise recommendation that will result in the user burning 500 calories during the exercise.

Next, the user health goals module 216 is configured to output the recommendation 218 on the graphical user interface 222, by sending the recommendation 218 to the graphical user interface module 220. As described above, the graphical user interface module 220 is configured to display the graphical user interface 222 including the indicator of the calorie count statistic 224 and the recommendation 218 on the display 226 associated with the client computing device 12.

Figure 3:
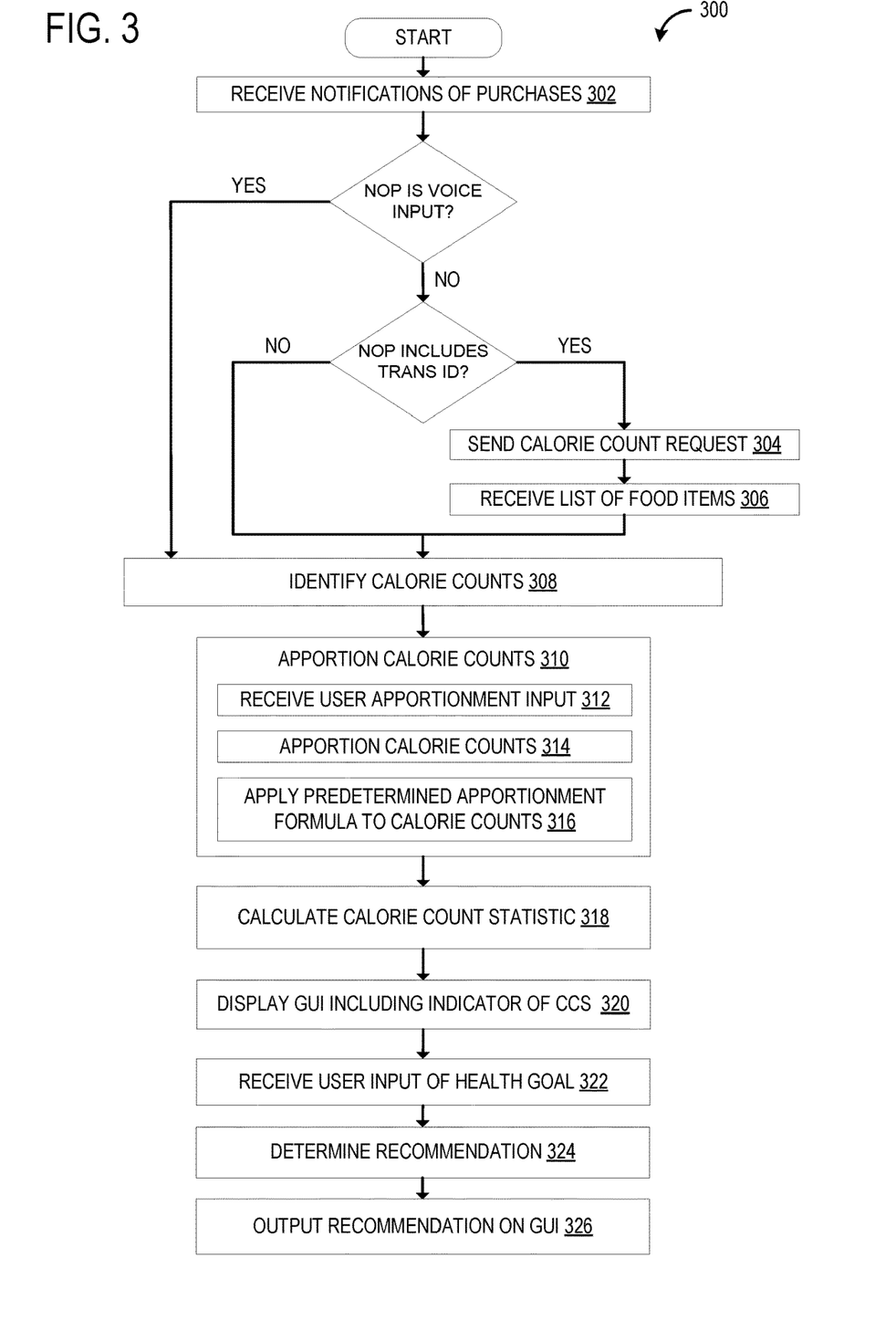
FIG. 3 shows an example method for calculating a calorie count statistic using the computing system of FIG. 1.

FIG. 3 shows an example method 300 for calculating a calorie count statistic. At step 302, the method 300 includes receiving notifications of purchases made for individual food items. In one embodiment, the notifications of purchases are voice inputs received from the user that indicate a purchased food item. In another embodiment, the notifications of purchases are electronic receipts received from a food vendor, the electronic receipts including a cost and a calorie count for each purchased food item. In another embodiment, the notifications of purchases are electronic receipts that include a transaction identifier. As discussed above, the electronic receipts may be received by via a near field connection, via a payment card transaction server, via an email message, via a text message, or via an in-app message as a few non-limiting examples.

If the notifications of purchases are voice inputs received from the user that indicate a purchased food item, the method 300 proceeds from step 302 to step 308. At step 308 the method 300 may include identifying calorie counts associated with each purchased food item indicated by the voice input received from the user according to the methods described previously.

If the notification of purchases are electronic receipts that include a transaction identifier, the method 300 proceeds from step 302 to step 304, and includes sending a calorie count request to a calorie count server including the transaction identifier. The method 300 advances from step 304 to step 306, and includes receiving, from the calorie count server, a list of food items associated with the transaction identifier and calorie counts for each food item in the list. Next, the method 300 proceeds from step 306 to step 308.

If the notification of purchases are electronic receipts that do not include a transaction identifier, but does include the calorie counts of the food items, then the method 300 proceeds from step 302 directly to step 308. At step 308, the method 300 includes identifying calorie counts associated with each purchased food item.

Advancing from step 308 to step 310, the method 300 includes apportioning the calorie counts of the food items to a user. Step 308 includes substeps 312-316. At substep 312, the method 300 includes receiving a user apportionment input. At substep 314, the method 300 includes apportioning the calorie counts by the user apportionment input. At substep 316, the method 300 includes applying a predetermined apportionment formula to the calorie counts, so that the calorie count statistic reflects the apportioned total of the calorie counts of the food items that have been apportioned to the user.

Proceeding from step 310 to step 318, the method 300 includes calculating a calorie count statistic based thereon. The calorie count statistic may be, for example, a total calorie count during a time period, an average calorie count during a repeating time period, or a remaining calorie count until a maximum or minimum threshold is reach for a time period. In one embodiment, calculating a total calorie count comprises calculating the total calorie count for a user-specified period of time, such as 2 hours, 6 hours, a day, a week, or a month as a few non-limiting examples.

Advancing from step 318 to step 320, the method 300 includes displaying a graphical user interface including an indicator of the calorie count statistic.

Proceeding from step 320 to step 322, the method 300 includes receiving user input of a health goal from a user. It will be appreciated that the health goal may be inputted through a variety of methods, such as a voice input, a touch input, or a gesture input as a few non-limiting examples.

Advancing from step 322 to step 324, the method 300 includes determining a recommendation based upon the user inputted health goal and the calorie count statistic. In one embodiment, the recommendation is a food item recommendation or an exercise recommendation. In this embodiment, the food item recommendation is determined based upon user profile data associated with a user profile, the recommendation including a food item recommendation that is further determined based upon user profile data associated with a user profile, the user profile data including nutrition behavior and patterns of the user determined based on a history of purchased food items and associated food vendors. Lastly, proceeding from step 324 to step 326, the method 300 includes outputting the recommendation on the graphical user interface.

Figure 4:
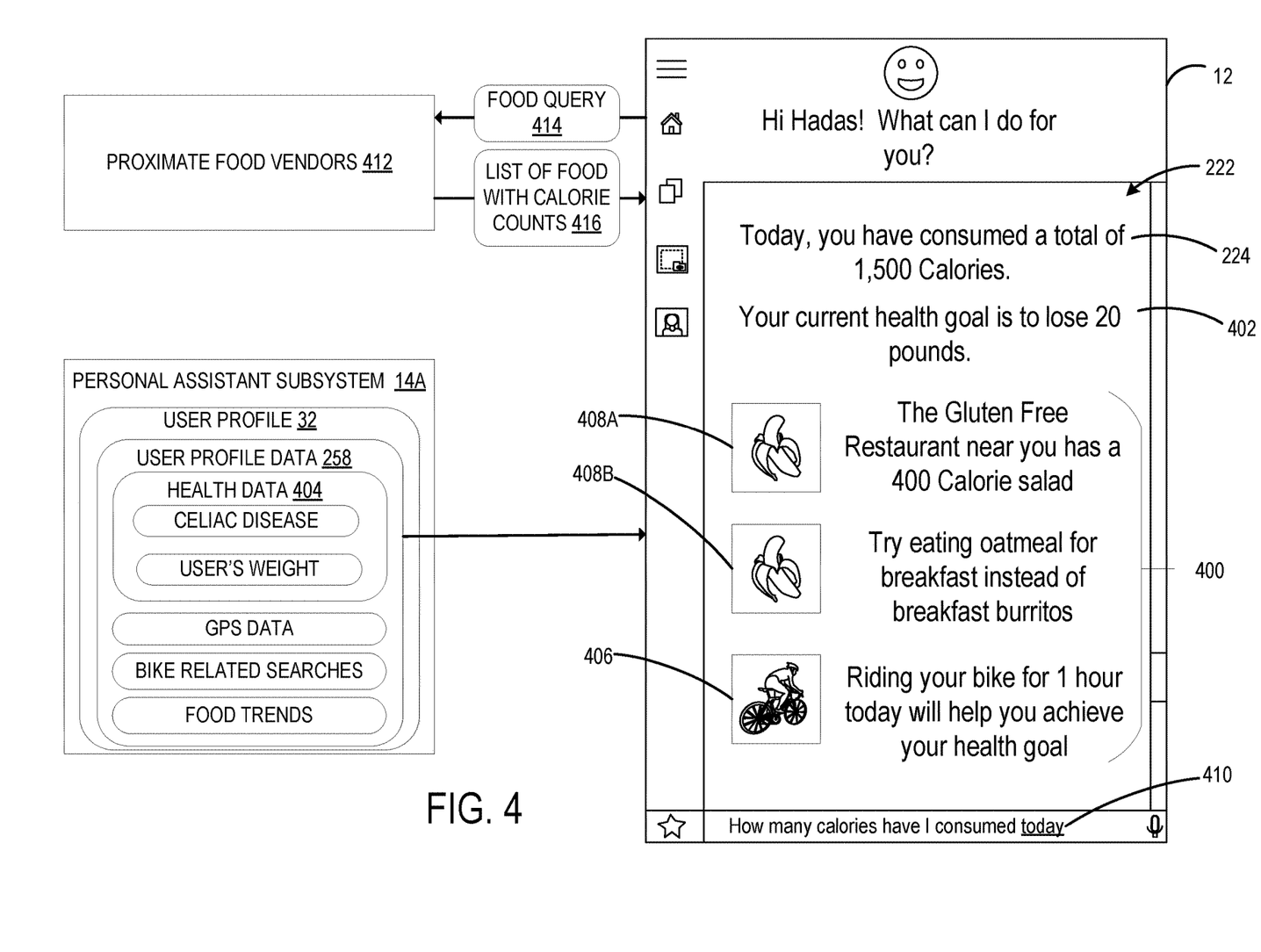
FIG. 4 shows an example client computing device of the computing system of FIG. 1.

Now turning to FIG. 4, an example client computing device 12 and a graphical user interface 222 is illustrated. The graphical user interface 222 includes the indicator of the calorie count statistic 224, as well as a set of recommendations 400. In the illustrated example, the total calorie count was calculated for the user specified time period 410 of a day. As shown, the user specified this time period when the user asked "How many calories have I consumed today?" to a microphone input device of the client computing device 12. However, it will be appreciated that the user may specify the time period through other methods, such as selecting a time period in a drop down menu via a touch input. Further, as an alternative example, the user may query "How many calories do I consume each Thanksgiving?" or "How many calories do I consume for lunch each weekday?" or "How many calories may I consume for the rest of the day before reaching my daily target limit?" and appropriate answers would be generated.

Additionally, in the illustrated example, the set of recommendations 400 were determined based on a user inputted health goal, which is shown in the illustrated example via an indicator of the health goal 402. In this example, the user's health goal is to lose 20 pounds. Based on the user's current weight that the client computing device 12 may retrieve from the health data 404 included in the user's profile data 258, the client computing device 12 may determine that the user needs to eat less than 2000 calories a day in order to lose weight and achieve the user inputted health goal of losing 20 pounds. Thus, the client computing device 12 may output recommendations 400 that include food item recommendations 408A and 408B and an exercise recommendation 406.

As illustrated, the exercise recommendation 406 is a recommendation for the user to bike for an hour. This exercise recommendation may be determined based on the user profile data 32 which may include trends of the user's inputs to search engines. As illustrated, the user frequently searches for bike related information. Thus, to appeal to the user's known interest in bikes, the client computing device 12 may determine the exercise recommendation 406 to be a recommendation to ride a bike.

The food recommendations 408A and 408B may be determined based on the health data 404 of the user profile data 32, the user's calorie count statistic, as well as food available from proximate food vendors near the user. The client computing device 12 may retrieve the available food by sending food queries 414 to the proximate food vendors 412, and receive lists of food with calorie counts 416 from the proximate food vendors. In the illustrated example, the client computing device 12 determines the food recommendation 408A based on the health data 404 that indicates that the user has Celiac Disease, the total calorie count 1500 calories, and the received lists of food with calories counts 416. Thus, the client computing device 12 outputs the recommendation 408A that "The Gluten Free Restaurant" near the user has a 400 calorie salad that satisfies the user's health condition as well as the user's health goal.

As illustrated in FIG. 4, the client computing device 12 also outputs a second food recommendation 408B, which is a food recommendation aimed to change the user's eating habits in order to achieve the user inputted health goal. As shown, the user profile data 258 may include food trend data which may be used by the client computing device 12 to determine food recommendations. In the illustrated example, the client computing device 12 determines that the user tends to eat breakfast burritos, which have a high calorie count. Thus, the client computing device 12 determines the food recommendation 408B that suggests oatmeal as an alternative breakfast meal that will help the user achieve the user inputted health goal of losing 20 pounds.

Figure 5:
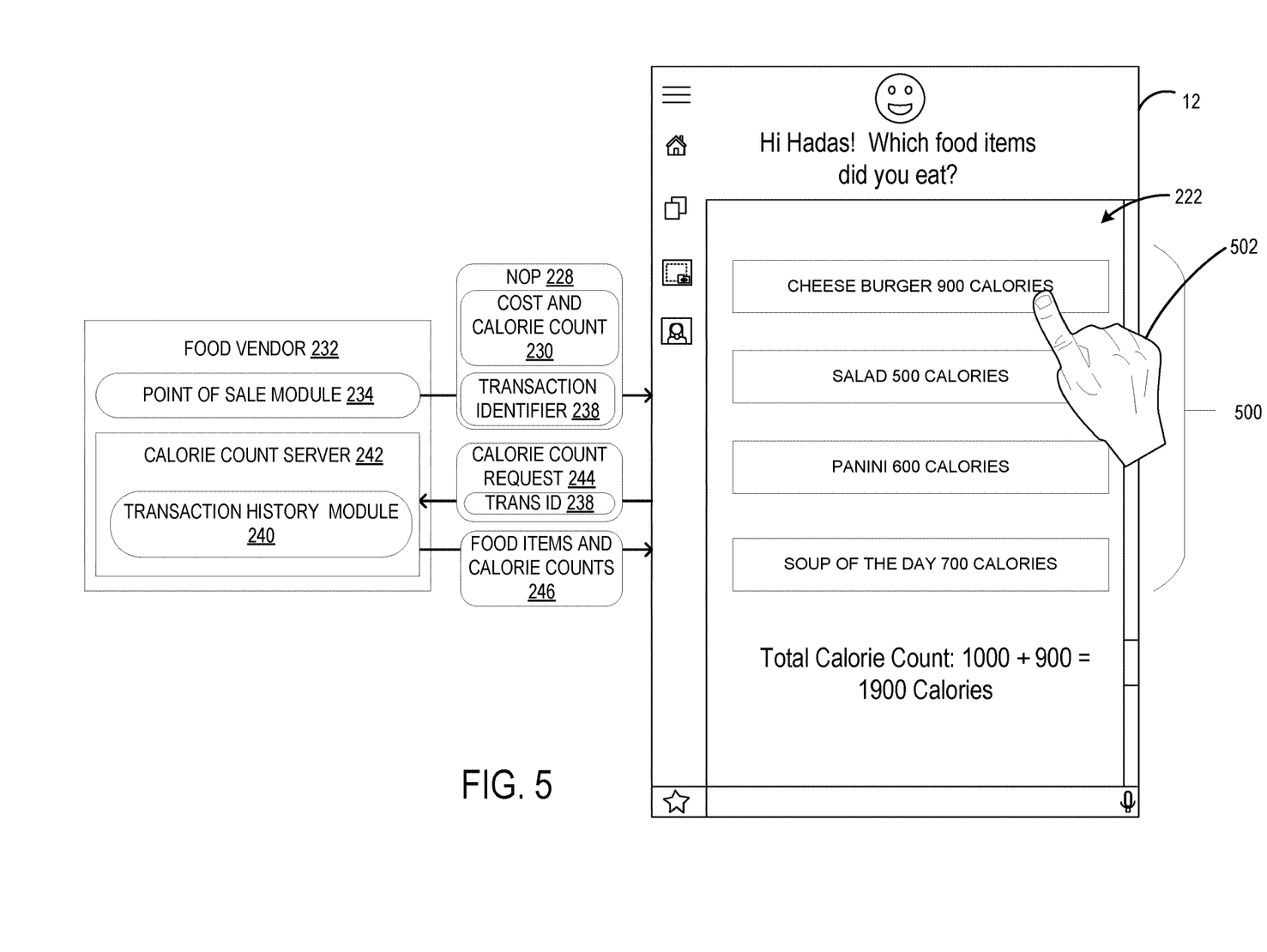
FIG. 5 shows an example client computing device of the computing system of FIG. 1.

FIG. 5 illustrates an example of apportioning calorie counts to the user based on a user apportionment input. As illustrated, the client computing device 12 receives food items and calorie counts 246 from the food vendor 232. The client computing device 12 outputs the list of food items to the graphical user interface 222 as an itemized list of selectable food items 500. The user may then select the food items that the user ate via a user apportionment input. In the illustrated example, the user enters the user apportionment input via a touch input 502, selecting the cheese burger food item for the list of selectable food items. The client computing device 12 then applied the predetermined apportionment formula to the calorie counts, which in the illustrated example is adding the calorie count of the selected food item to the total calorie counts of the user. As shown, the calorie count of the cheese burger of 900 Calories is directly added to the total calorie count for the user and displayed on the graphical user interface 222.

In some embodiments, the methods and processes described herein may be tied to a computing system of one or more computing devices. In particular, such methods and processes may be implemented as a computer-application program or service, an application-programming interface (API), a library, and/or other computer-program product.

Figure 6:
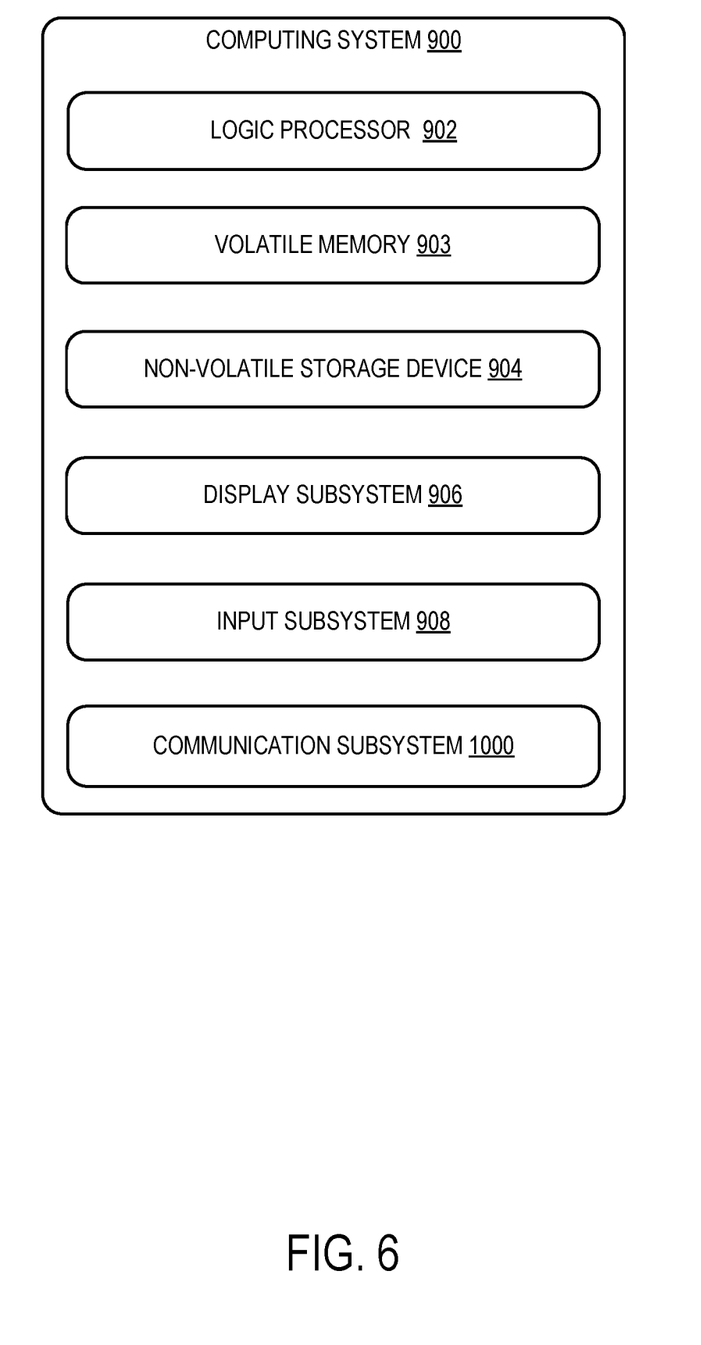
FIG. 6 shows an example computing system according to an embodiment of the present description.

FIG. 6 schematically shows a non-limiting embodiment of a computing system 900 that can enact one or more of the methods and processes described above. Computing system 900 is shown in simplified form. Computing system 900 may embody one or more of the servers or client computing devices 12 or other computing devices 16 of FIG. 1. Computing system 900 may take the form of one or more personal computers, server computers, tablet computers, home-entertainment computers, network computing devices, gaming devices, mobile computing devices, mobile communication devices (e.g., smart phone), and/or other computing devices, wearable computing devices such as smart wristwatches and head mounted augmented reality devices, computerized medical devices.

Computing system 900 includes a logic processor 902 volatile memory 903, and a non-volatile storage device 904. Computing system 900 may optionally include a display subsystem 906, input subsystem 908, communication subsystem 1000, and/or other components not shown in FIG. 6.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 904 includes one or more physical devices configured to hold instructions executable by the logic processors to implement the methods and processes described herein. When such methods and processes are implemented, the state of non-volatile storage device 94 may be transformed—e.g., to hold different data.

Non-volatile storage device 904 may include physical devices that are removable and/or built-in. Non-volatile storage device 94 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 904 may include nonvolatile, dynamic, static, read/write, read-only, sequential-access, location-addressable, file-addressable, and/or content-addressable devices. It will be appreciated that non-volatile storage device 904 is configured to hold instructions even when power is cut to the non-volatile storage device 904.

Volatile memory 903 may include physical devices that include random access memory. Volatile memory 903 is typically utilized by logic processor 902 to temporarily store information during processing of software instructions. It will be appreciated that volatile memory 903 typically does not continue to store instructions when power is cut to the volatile memory 903.

Aspects of logic processor 902, volatile memory 903, and non-volatile storage device 904 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 900 typically implemented in software by a processor to perform a particular function using portions of volatile memory, which function involves transformative processing that specially configures the processor to perform the function. Thus, a module, program, or engine may be instantiated via logic processor 902 executing instructions held by non-volatile storage device 904, using portions of volatile memory 903. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 906 may be used to present a visual representation of data held by non-volatile storage device 904. The visual representation may take the form of a graphical user interface (GUI). As the herein described methods and processes change the data held by the non-volatile storage device, and thus transform the state of the non-volatile storage device, the state of display subsystem 906 may likewise be transformed to visually represent changes in the underlying data. Display subsystem 906 may include one or more display devices utilizing virtually any type of technology. Such display devices may be combined with logic processor 902, volatile memory 903, and/or non-volatile storage device 904 in a shared enclosure, or such display devices may be peripheral display devices.

When included, input subsystem 908 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 1000 may be configured to communicatively couple various computing devices described herein with each other, and with other devices. Communication subsystem 1000 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 900 to send and/or receive messages to and/or from other devices via a network such as the Internet.

The following paragraphs provide additional support for the claims of the subject application. One aspect provides a computing system, comprising: an electronic personal assistant application program executed on a client computing device, and including: a purchase tracking module configured to receive notifications of purchases made for individual food items, a calorie tracking module configured to identify calorie counts associated with each purchased food item and to calculate a calorie count statistic based thereon, a calorie apportionment module configured to apportion the calorie counts of the food items to a user by receiving a user apportionment input and apportioning the calorie counts by the user apportionment input, and applying a predetermined apportionment formula to the calorie counts, so that the calorie count statistic is based upon an apportioned total of the calorie counts of the food items that have been apportioned to the user, and a graphical user interface module configured to display a graphical user interface including an indicator of the calorie count statistic on a display associated with the client computing device. In this aspect, the computing system may additionally or alternatively include, wherein the graphical user interface module is further configured to display an itemized list of the food items and associated calorie counts, and wherein the user apportionment input is a user selection input of a food item. In this aspect, the computing system may additionally or alternatively include, wherein the user apportionment input is a user input of a ratio of the food items consumed by the user. In this aspect, the computing system may additionally or alternatively include, wherein the user apportionment input is a user input of a list of people that consumed the food items, and wherein the predetermined apportionment formula is a ratio of the user's body weight compared to a total body weight of the list of people. In this aspect, the computing system may additionally or alternatively include, wherein the notifications of purchases are electronic receipts that include a cost and a calorie count for each purchased food item. In this aspect, the computing system may additionally or alternatively include, wherein the notifications of purchases are electronic receipts that include a transaction identifier, and wherein the calorie tracking module is configured to send a calorie count request to a calorie count server including the transaction identifier, and receive from the calorie count server a list of food items associated with the transaction identifier and calorie counts for each food item in the list. In this aspect, the computing system may additionally or alternatively include, wherein the notifications of purchases are voice inputs from the user that indicate a purchased food item. In this aspect, the computing system may additionally or alternatively include, the electronic personal assistant application program further including a user health goals module configured to: receive user input of a health goal from a user, determine a recommendation based upon the user inputted health goal and the calorie count statistic, and output the recommendation on the graphical user interface. In this aspect, the computing system may additionally or alternatively include, wherein the recommendation is a food item recommendation or an exercise recommendation. In this aspect, the computing system may additionally or alternatively include, wherein the food item recommendation is further determined based upon user profile data associated with a user profile, the user profile data including nutrition behavior and patterns of the user determined based on a history of purchased food items and associated food vendors. In this aspect, the computing system may additionally or alternatively include, wherein the food item recommendation is further determined based upon availability of food items from vendors in proximity to the user's expected location at a next meal time.

Another aspect provides a method, comprising: receiving notifications of purchases made for individual food items, identifying calorie counts associated with each purchased food item, calculating a calorie count statistic based thereon, apportioning the calorie counts of the food items to a user by receiving a user apportionment input and apportioning the calorie counts by the user apportionment input, and applying a predetermined apportionment formula to the calorie counts, so that the calorie count statistic is based upon an apportioned total of the calorie counts of the food items that have been apportioned to the user, and displaying a graphical user interface including an indicator of the total calorie count. In this aspect, the method may additionally or optionally include, displaying an itemized list of the food items and associated calorie counts, and wherein the user apportionment input is a user input of a selection of a food item. In this aspect, the method may additionally or optionally include, wherein the user apportionment input is a user input of a ratio of the food items consumed by the user. In this aspect, the method may additionally or optionally include, wherein the user apportionment input is a user input of a list of people that consumed the food items, and wherein the predetermined apportionment formula is a ratio of the user's body weight compared to a total body weight of the list of people. In this aspect, the method may additionally or optionally include, wherein the notifications of purchases are electronic receipts received from a food vendor, the electronic receipts including a cost and a calorie count for each purchased food item. In this aspect, the method may additionally or optionally include, wherein the notifications of purchases are electronic receipts that include a transaction identifier, and wherein the method further comprises: sending a calorie count request to a calorie count server including the transaction identifier, and receiving, from the calorie count server, a list of food items associated with the transaction identifier and calorie counts for each food item in the list. In this aspect, the method may additionally or optionally include, wherein the notifications of purchases are voice inputs received from the user that indicate a purchased food item. In this aspect, the method may additionally or optionally include, receiving user input of a health goal from a user, determining a recommendation based upon the user inputted health goal and the total calorie count, the recommendation including a food item recommendation that is further determined based upon user profile data associated with a user profile, the user profile data including nutrition behavior and patterns of the user determined based on a history of purchased food items and associated food vendors, and outputting the recommendation on the graphical user interface.

Another aspect provides a computing system comprising: a display device configured to display a graphical user interface, and a processor configured to: receive notifications of purchases made for individual food items, identify calorie counts associated with each purchased food item, calculate a total calorie count based thereon, apportion the calorie counts of the food items to a user by receiving a user apportionment input and apportioning the calorie counts by the user apportionment input, and applying a predetermined apportionment formula to the calorie counts, so that the calorie count statistic is based upon an apportioned total of the calorie counts of the food items that have been apportioned to the user, receive user input of a health goal, determine a recommendation based upon the user inputted health goal and the total calorie count, and display, via the graphical user interface of the display device, an indicator of the total calorie count and the recommendation.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing system, comprising:
   an electronic personal assistant application program executed on a client computing device, and including:
   a personal assistant subsystem configured to manage a user profile for a user of the computing system, the user profile including location trends for the user determined based on global positioning system (GPS) data including a plurality of detected GPS locations of the user;
   a purchase tracking module configured to receive notifications of purchases made for individual food items;
   a calorie tracking module configured to identify calorie counts associated with each purchased food item and to calculate a calorie count statistic based on the identified calorie counts;
   a user health goals module configured to receive user input of a health goal from the user and determine a recommendation based upon the user inputted health goal and the calorie count statistic, the recommendation including a food item recommendation determined at least based upon availability of food items from vendors in proximity to an expected location of the user at a next meal time, the expected location of the user at the next meal time being determined based on at least the determined location trends of the user stored in the user profile for the user; and
   a graphical user interface module configured to display a graphical user interface including an indicator of the calorie count statistic on a display associated with the client computing device and output the recommendation on the graphical user interface.

2. The computing system of claim 1, wherein the recommendation further includes an exercise recommendation.

3. The computing system of claim 1, wherein the food item recommendation is further determined based upon user profile data associated with the user profile, the user profile data including nutrition behavior and patterns of the user determined based on a history of purchased food items and associated food vendors.

4. The computing system of claim 1, wherein the notifications of purchases are electronic receipts that include a cost and a calorie count for each purchased food item.

5. The computing system of claim 1, wherein the notifications of purchases are voice inputs from the user that indicate a purchased food item.

6. The computing system of claim 3, wherein the food item recommendation is further determined based upon user medical data included in the user profile.

7. The computing system of claim 1, wherein the notifications of purchases are electronic receipts that include a transaction identifier; and
wherein the calorie tracking module is configured to:
send a calorie count request to a calorie count server including the transaction identifier, and
receive from the calorie count server a list of food items associated with the transaction identifier and calorie counts for each food item in the list.

8. The computing system of claim 1, wherein the electronic personal assistant application program further includes a calorie apportionment module configured to:
apportion the calorie counts of the food items to the user by receiving a user apportionment input and apportioning the calorie counts by the user apportionment input, and
apply a predetermined apportionment formula to the calorie counts, so that the calorie count statistic is based upon an apportioned total of the calorie counts of the food items that have been apportioned to the user.

9. The computing system of claim 8, wherein the user apportionment input includes a user input of a list of people that consumed the food items, each person in the list of people having respective user profiles stored on a server system associated with the electronic personal assistant application program, and
wherein the calorie apportionment module is configured to apportion the calorie counts of the food items to the user based on at least health data included in respective user profiles retrieved from the server system for the list of people and the predetermined apportionment formula.

10. The computing system of claim 9, wherein the predetermined apportionment formula is a ratio of the user's body weight compared to a total body weight of the list of people.

11. A method, comprising:
at a processor of a computing system:
managing a user profile for a user of the computing system, the user profile including location trends for the user determined based on global positioning system (GPS) data including a plurality of detected GPS locations of the user;
receiving notifications of purchases made for individual food items, wherein the notifications of purchases includes at least one of an electronic receipt received by the computing system over a communication network or a user input received via a user input device of the computing system;
identifying calorie counts associated with each purchased food item indicated in the notifications of purchases and calculating a calorie count statistic based on the identified calorie counts;
receiving user input of a health goal from the user via the user input device of the computing system and determining a recommendation based upon the user inputted health goal and the calorie count statistic, the recommendation including a food item recommendation determined at least based upon availability of food items from vendors in proximity to an expected location of the user at a next meal time, the expected location of the user at the next meal time being determined based on at least the determined location trends of the user stored in the user profile for the user; and
displaying a graphical user interface including an indicator of the calorie count statistic on a display associated with the computing system and outputting the recommendation on the graphical user interface.

12. The method of claim 11, wherein the recommendation further includes an exercise recommendation.

13. The method of claim 11, wherein the food item recommendation is further determined based upon user profile data associated with the user profile, the user profile data including nutrition behavior and patterns of the user determined based on a history of purchased food items and associated food vendors.

14. The method of claim 13, wherein the food item recommendation is further determined based upon user medical data included in the user profile.

15. The method of claim 11, wherein the notifications of purchases are electronic receipts that include a cost and a calorie count for each purchased food item.

16. The method of claim 11, wherein the notifications of purchases are voice inputs from the user that indicate a purchased food item.

17. The method of claim 11, wherein the notifications of purchases are electronic receipts that include a transaction identifier; and
wherein the method further comprises:
sending a calorie count request to a calorie count server including the transaction identifier, and
receiving from the calorie count server a list of food items associated with the transaction identifier and calorie counts for each food item in the list.

18. The method of claim 11, further comprising:
apportioning the calorie counts of the food items to the user by receiving a user apportionment input and apportioning the calorie counts by the user apportionment input, and
applying a predetermined apportionment formula to the calorie counts, so that the calorie count statistic is based upon an apportioned total of the calorie counts of the food items that have been apportioned to the user.

19. The method of claim 18, wherein the user apportionment input includes a user input of a list of people that consumed the food items, each person in the list of people having respective user profiles, and
wherein the method further comprises apportioning the calorie counts of the food items to the user based on at least health data included in respective user profiles for the list of people and the predetermined apportionment formula.

20. The method of claim 19, wherein the predetermined apportionment formula is a ratio of the user's body weight compared to a total body weight of the list of people.

* * * * *